United States Patent [19]
Willy et al.

[11] 3,958,010
[45] May 18, 1976

[54] MITE CONTROL

[75] Inventors: William E. Willy; Clive A. Henrick, both of Palo Alto, Calif.

[73] Assignee: Zoecon Corporation, Palo Alto, Calif.

[22] Filed: Mar. 6, 1975

[21] Appl. No.: 555,757

[52] U.S. Cl.................................. 424/318; 424/317
[51] Int. Cl.$^2$............................................. A01N 9/24
[58] Field of Search............................ 424/317, 318

[56] References Cited
UNITED STATES PATENTS
3,578,685  5/1971  Archer................................ 260/396

OTHER PUBLICATIONS

Slama, Annual Review of Biochemistry, pp. 1079, 1096 & 1097, (1971).

Toubiana et al., Chem. Abst., Vol. 56, 1962, pp. 10676–10677.

*Primary Examiner*—Sam Rosen
*Assistant Examiner*—Allen J. Robinson
*Attorney, Agent, or Firm*—Donald W. Erickson

[57] ABSTRACT

Cyclopropyl substituted carboxylic acids are useful for the control of spider mites.

5 Claims, No Drawings

MITE CONTROL

This invention relates to the use of cyclopropyl substituted carboxylic acids for the control of spider mites.

It has now been found that acids of Formula I are useful for the control of spider mites

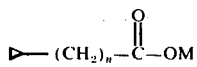  (I)

wherein;

n is an even integer between 6 and 14; and

M is hydrogen, ammonium or a metal cation.

The compounds of Formula I can be applied to the spider mite at all stages of its development, namely during the egg, larvae, nymphal, and adult stages, thereby causing inability to pass from one stage to the next or inability to reproduce.

A compound of formula I, or mixtures thereof, can be applied at dosage levels of the order of 0.001% to 1%. Suitable carrier substances include liquid or solid inert carriers, such as water, acetone, xylene, mineral or vegetable oils, talc, vermiculite, and silica. Treatment of mites in accordance with the present invention can be accomplished by spraying, dusting, or otherwise contacting the mites and/or their eggs or larvae directly or indirectly. Generally, a concentration of less than 25% of active compound is employed, although higher concentrations of the active compound can be used depending on the type of application and effectiveness of the active ingredient.

The compounds of Formula I can be prepared using the method of U.S. Pat. No. 3,578,685 or the method of copending Ser. No. 489,207, filed July 17, 1974, the disclosure of which is hereby incorporated by reference.

Salts of the acids of formula I are prepared using conventional techniques well-known in the art. For example, the ammonium salt is prepared by treating the acid with ammonia gas; the metal salt, such as the sodium, potassium, lithium, or calcium salt, is prepared from the free acid and the appropriate metal hydride, etc.

The acids included in formula I are the following:
7-cyclopropylheptanoic acid
9-cyclopropylnonanoic acid
11-cyclopropylundecanoic acid
13-cyclopropyltridecanoic acid
15-cyclopropylpentadecanoic acid The miticidal activity of these acids is illustrated by the following test:

Adult mites (*Tetranychus urticae*) were allowed to oviposit for 24 hours on the upper side of lima bean leaf discs (1 cm.) on moist cotton wool. After twenty-four hours, the adults were removed and the leaf discs were then dipped in acetone solutions of the compound to be tested. After submersion for about one second, the solvent on the leaf discs is allowed to evaporate and the leaf discs are then glued to a plastic petri dish to prevent crumpling. Five days later, the number of unhatched eggs (mortality) is calculated as a percentage of the total number originally present, corrected for any spontaneous non-emergence observed in control discs treated only with solvent (Abbott correction).

Table I presents the results of this miticidal testing.

Table 1

| Compound | % concentration in solution | % hatching prevented |
|---|---|---|
| 7-cyclopropylheptanoic acid | 0.1 | 100 |
| 9-cyclopropylnonanoic acid | 0.1 | 100 |
| 11-cyclopropylundecanoic acid | 0.1 | 100 |

The acids of the present invention can be used alone or in an inert carrier substance for the control of mites (Acarina) or can be used in a mixture with pesticides, miticides, especially adulticides, and/or juvenile hormone analogs known in the art in order to obtain a broader spectrum of activity. Suitable miticices and insecticides include Plictran, Omite, Baygon, Captan, Sevin, Ciodrin, Systox, Diazinon, Vapona, Galecron, Cygon, Dimethrin, Dursban, Malathion, and Parathion. Typical juvenile hormone analogs which can be used in mixture with the compound of the present invention are described in U.S. Pat. Nos. 3,752,843 and 3,755,411.

A wettable powder suitable for field application after dilution can be formulated by blending and then air-milling a mixture of about 20 to 30% of a compound of formula I of this invention, 60 to 70% of a solid carrier such as Attaclay X-250, 1 to 3% of an anionic surfactant, such as Igepon T-77, and 3 to 5% of a dispersing agent such as Marasperse N-22.

What is claimed is:

1. A method for controlling spider mites which comprises applying to the eggs of the spider mite, an ovicidally effective amount of a compound of the formula

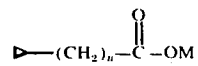

wherein n is an even integer of 6 to 14 and M is hydrogen, ammonium, lithium, potassium, sodium or calcium.

2. The method according to claim 1 wherein n is 6, 8 or 10 and M is hydrogen.

3. The method according to claim 1 wherein the compound is 7-cyclopropylheptanoic acid.

4. The method according to claim 1 wherein the compound is 9-cyclopropylnonanoic acid.

5. The method according to claim 1 wherein the compound is 11-cyclopropylundecanoic acid.

* * * * *